United States Patent
Hancock et al.

(10) Patent No.: US 8,500,726 B2
(45) Date of Patent: Aug. 6, 2013

(54) ELECTROSURGICAL ABLATION APPARATUS AND A METHOD OF ABLATING BIOLOGICAL TISSUE

(75) Inventors: Christopher P. Hancock, Bristol (GB); Mohammed Sabih Chaudry, Gwynedd (GB); Christopher Duff, Leyland (GB)

(73) Assignee: Medical Device Innovations Limited, Halton, Cheshire (GB)

( * ) Notice: Subject to any disclaimer, the term of this patent is extended or adjusted under 35 U.S.C. 154(b) by 824 days.

(21) Appl. No.: 12/517,516

(22) PCT Filed: Dec. 3, 2007

(86) PCT No.: PCT/GB2007/004633
§ 371 (c)(1),
(2), (4) Date: Jan. 7, 2010

(87) PCT Pub. No.: WO2008/071914
PCT Pub. Date: Jun. 19, 2008

(65) Prior Publication Data
US 2010/0145328 A1    Jun. 10, 2010

(30) Foreign Application Priority Data
Dec. 11, 2006 (GB) .................................. 0624658.1

(51) Int. Cl.
*A61B 18/18* (2006.01)
(52) U.S. Cl.
USPC .............................................. 606/33; 606/32
(58) Field of Classification Search
USPC ..................................................... 606/32–45
See application file for complete search history.

(56) References Cited

U.S. PATENT DOCUMENTS

| 4,878,493 A | 11/1989 | Pasternak et al. |
| 5,800,494 A | 9/1998 | Campbell et al. |
| 5,906,609 A * | 5/1999 | Assa et al. ..................... 606/9 |
| 6,039,734 A * | 3/2000 | Goble ............................. 606/41 |
| 6,463,336 B1 | 10/2002 | Mawhinney |

(Continued)

FOREIGN PATENT DOCUMENTS

| EP | 1 669 036 A | 6/2006 |
| GB | 2388039 A | 11/2003 |

(Continued)

OTHER PUBLICATIONS

English Language JPO Office Action dated Jun. 5, 2012.

(Continued)

*Primary Examiner* — Linda Dvorak
*Assistant Examiner* — Amanda Scott
(74) *Attorney, Agent, or Firm* — Arent Fox LLP

(57) ABSTRACT

A portable electrosurgical system (100) for treating biological tissue with microwave radiation (e.g. having a frequency between 500 MHz and 60 GHz) is disclosed. The system comprises a hand-held microwave sub-assembly (102) which generates and amplifies a microwave signal (which may be continuous or modulated) for treatment and includes a treatment antenna (116) for delivering the radiation. Diode detectors (120, 122) in the sub-assembly (102) may detect forward and reflected power levels to enable determination of net delivered power. A dynamic impedance matching system may be provided to match energy developed by amplifiers (110, 112) in the sub-assembly (102) to the biological tissue load. A tuning filter (144) and couplers (146, 148, 150, 152) for extracting magnitude and phase information from the microwave signal are thus provided in the sub-assembly.

18 Claims, 7 Drawing Sheets

U.S. PATENT DOCUMENTS

2001/0025190 A1* 9/2001 Weber et al. ............ 607/89
2006/0155270 A1* 7/2006 Hancock et al. ............ 606/33
2008/0234574 A1 9/2008 Hancock et al.

FOREIGN PATENT DOCUMENTS

| GB | 2403148 A | 12/2004 |
| GB | 2416307 A | 1/2006 |
| GB | 2434314 A | 7/2007 |
| JP | 10-216139 A | 8/1998 |
| JP | 2004-129847 A | 4/2004 |
| WO | WO 93/20768 A1 | 10/1993 |
| WO | WO 01/03594 A1 | 1/2001 |
| WO | WO 2004/047659 A | 6/2004 |
| WO | WO 2004/047695 A | 6/2004 |
| WO | WO 2005/110272 A | 11/2005 |
| WO | WO 2005/115235 A | 12/2005 |
| WO | WO 2006/053309 A2 | 5/2006 |
| WO | WO 2006/084676 A | 8/2006 |
| WO | WO 2006/095171 A1 | 9/2006 |

OTHER PUBLICATIONS

UKIPO Search Report on GB 0624658.1 dated Apr. 12, 2007.
UKIPO Search Report on GB 0624658.1 dated Aug. 24, 2007.
English Language SIPO First Office Action on CN 200780049726.2 dated Jun. 11, 2010.
English Language SIPO Second Office Action on CN 200780049726.2 dated Dec. 14, 2010.
English Language SIPO Third Office Action on CN 200780049726.2 dated Dec. 21, 2011.

* cited by examiner

ELECTROSURGICAL ABLATION APPARATUS AND A METHOD OF ABLATING BIOLOGICAL TISSUE

CROSS-REFERENCE TO RELATED APPLICATION

This application is a National Stage entry of International Application No. PCT/GB2007/046333, having international filing date of Dec. 3, 2007, which claims priority to GB Patent Application No. 0624658.1 filed Dec. 11, 2006, the disclosure of each of which is hereby incorporated in its entirety by reference.

FIELD OF THE INVENTION

The invention relates to apparatus for and methods of using microwave radiation in the treatment of biological tissue.

BACKGROUND TO THE INVENTION

Microwave energy having a frequency between 14 GHz and 15 GHz can produce controlled ablation of biological tissue. At these frequencies, the depth of penetration of the radiation is limited, which may be beneficial.

WO 2004/047659 and WO 2005/115235 disclose apparatus for and methods of both ablating tissue and measuring information about tissue type and/or state using microwave radiation. These documents disclose the benefits of performing dynamic impedance matching between the energy source and the tissue.

These documents address the disadvantage of using RF and low frequency microwave treatment systems, where the dominant energy transport mechanism is thermal conduction and the depth of penetration (defined herein as being the distance the energy has spread when the energy source has reduced to 37% of the maximum value) is such that a large mass of tissue is heated before the temperature of the target tissue can be elevated to the required value.

SUMMARY OF THE INVENTION

The current invention desirably builds on the systems disclosed in WO 2004/047659 and WO 2005/115235. Expressed generally, the invention provides a portable device for delivering energy produced at microwave frequencies to produce controlled ablation with desirable depths of penetration by radiation to enable effective treatment of conditions relating to small tissue structures, for example, thread veins, warts, skin tags and moles. The device may be suitable for use in situations where it is difficult to access the treatment site or in awkward (unsuitable) treatment conditions. For example, possible applications include car accident casualty treatment, battle field injury treatment, sealing to prevent excessive blood loss during general surgery and use by veterinary surgeons to prevent excessive blood loss to animals.

The ability to stop wound bleeding using a system that does not require a mains voltage supply may be particularly attractive to paramedics or military surgeons operating in the field where loss of blood due to war wounds or accident injury is potentially life threatening. A system that combines portability together with the ability to generate high frequency microwave energy is particularly advantageous since high frequency microwave energy will instantly heat tissue to a temperature whereby effective cauterization or coagulation or ablation takes place. The use of high frequency microwave energy enables the energy to be delivered by non-ionising radiation rather than by thermal conduction and so the effect is virtually instantaneous.

Another advantage of the portable nature of the invention may be to avoid the long microwave cable assemblies connecting a microwave generator to a treatment antenna disclosed in WO 2004/047659 and WO 2005/115235. By avoiding this, the invention may permit measurements to be taken close to the tissue being treated, thereby eliminating undesirable effects of phase and magnitude variation with cable flexure. Moreover, a portion of the power generated by the microwave source that is transferred into the tissue using the hand held device can be optimised because it is not lost in the transmission cable. For example, if the delivery cable has an insertion loss of 3 dB then only half the power generated at the source arrives at the tissue load.

Accordingly, a first aspect of the invention may provide apparatus for treating biological tissue with microwave energy, the apparatus including a hand held unit having a microwave generator and an antenna, wherein the microwave generator is arranged to deliver microwave energy to the antenna wherefrom it is radiated to controllably ablate biological tissue. The hand held unit may have a pen-like geometry. The pen-like size enables the unit to be easily manipulated by a user, whilst preserving the advantages of having the microwave generator situated close to the antenna. In this case, the user may be any of the following individuals: medical consultant or surgeon, general practitioner, consultant, paramedic, military doctor or veterinary surgeon.

The apparatus may comprise two units. The first unit may be the hand held unit mentioned above. The hand held unit may be designed for a specific application, e.g. low power thread vein treatment or ligament tightening, or high power pain management (ablation of nerve plexi) or wound treatment. The second unit may be a control unit which includes a power supply (e.g. a DC power supply such as a battery pack or a switched mode power supply), control electronics (e.g. transistor turn-on/off sequencing circuit, and a shut-down system to turn off the microwave source when high levels of reflected power are encountered), and a user interface (e.g. status displays including bar display, micro-switches, LEDs, etc). The two units can be connected together using a low frequency cable assembly comprising DC power lines for taking power to the hand held unit (e.g. drain supply, gate-source supply, etc), and low frequency control signal lines for taking control signals between the hand held unit and the control unit (e.g. signals for forward and reflected power detectors, amplifier gain control, power level control, etc).

The invention arises in part from the realisation that small microwave engineering components are available at the frequencies which are of use for medical treatment. Also, new emerging device technologies, for example gallium nitride (GaN), enable higher microwave power to DC power efficiencies to be realised in practice. This invention discloses how such components may be arranged to create suitable electrosurgical devices.

Preferably, the microwave generator comprises a microwave frequency source, an amplifier (e.g. a monolithic microwave integrated circuit (MMIC) amplifier), a circulator, and a power dump load. Control of the microwave generator is achieved using sensing elements, which are arranged to detect the levels of forward and reflected power. The sensing results are fed as control signals to the control unit, which is arranged to control the microwave generator. The sensing elements are preferably provided in the hand held unit, but may be in the control unit. The sensing elements may comprise one or more microstrip line couplers (or E-field probes connected inside the microwave circulator to pick-up a small portion of forward and reflected power) and suitable diode detectors, for example, tunnel diodes, zero bias Schottky diodes, bolt channel Schottky diodes, or biased Schottky diodes. Alternatively, the sensing elements may comprise one or more waveguide couplers. An advantage of using a waveguide coupler is that the power loss through the structure (the insertion loss) is normally lower than that possible using a microstrip line coupler. Examples of suitable waveguide couplers include: the 'H'-loop coupler, the Riblet-Saad coupler, the Bethe-hole coupler, and the Schwinger reverse phase coupler.

The microwave generator preferably includes a modulation switch and an attenuator unit (e.g. controllable by the control unit) for pulsing the microwave power and controlling the power level respectively. It is preferable for the modulation switch and the attenuator to be inserted into the microwave line-up between the output of the frequency source and the input to the amplifier. In one embodiment, the modulation switch is a single pole single throw (SPST) PIN diode switch, and the attenuator is an eight bit 64 dB PIN diode digital attenuator or a 60 dB voltage variable attenuator.

Alternatively, the bias voltage supplied (e.g. from the control unit) to the MMIC amplifier or the discrete transistors used to form the power amplifier may be varied to control the power level. For example, GaAs power devices may be used to vary the gate-source voltage over a range that will enable the channel of the devices to be cut-off (drain current is zero) to where the channel is fully open and the device is operating in saturation (drain current is maximum). The shape of the transconductance curve associated with the particular device determines the values of gate-source voltage required to operate between zero and maximum drain current and it is possible to achieve a dynamic range for power control using this method of around 15 dB. This method of power control and switching (modulation) may be preferred for implementing power level control and pulsed power operation in the current invention where it is desirable to minimise the number of components to enable a physically small hand held unit to be realised. A further advantage associated with this power control regime is that the action of taking the gate-source voltage to pinch off the channel means that the DC power is also taken to zero, thus DC heating is minimised and microwave to DC power efficiency is maximised. It may be noted that operation using the normal class A biased configuration implies that a DC drain current (quiescent current) always flows even in the instance where no microwave energy is being generated; this method of taking the gate-source voltage to cut-off also ensures that the quiescent current is reduced to zero or close to zero (there may be some leakage current flowing, but this will have no significant effect since it will be of the order of micro-amperes or even nano-amperes).

If the microwave generator includes a modulation (e.g. SPST) switch and an attenuator unit, micro-electromechanical (MEM) switches may be used to implement the SPST switch. The advantage of using MEM devices is the superior reliability, and the small size. Existing MEM devices can operate at frequencies up to tens of GHz.

Operating the microwave generator in a pulsed mode may also optimise the efficiency of the device in terms of battery power consumption and may also prevent the hand held unit from getting excessively hot.

Microwave power to DC power efficiency may also be optimised by biasing the power devices used to form the output stage of the power amplifier in a configuration other than the standard class A bias. For example, class A-B, class B, class C, class D, class E, or class F may be considered. This invention is not limited to using the above mentioned classes of bias.

Preferably, the microwave generator is operable in two power modes: a high power mode suitable for ablation and a low power mode suitable for tissue type/state measurement. For the low power mode, it may be appropriate to use a high gain driver amplifier (e.g. an MMIC). For the high power mode, a series connected chain of amplifiers (or a plurality of suitable power transistor devices combined together using, for example, microwave power combiners (e.g. waveguide combiners or microstrip combiners)) can be used.

The range of microwave frequencies considered to be useful for the implementation of the current invention is between 500 MHz and 60 GHz. Specific frequency ranges that have been identified as being useful for implementation of the current invention are as follows: 2.4-2.45 GHz, 5.725-5.875 GHz, 14-15 GHz, and 24-24.25 GHz. Even more specifically, spot frequencies of 2.45 GHz, 5.8 GHz, 14.5 GHz, and 24 GHz are proposed. Frequencies around 915 MHz and 60 GHz may also be considered for future medical applications identified herein.

The choice of frequency depends on the tissue to be treated, the particular procedure to be performed, and the ability to generate sufficient microwave energy at the frequency of choice. Advances in semiconductor power technology make it possible to generate microwave power at the levels required to produce desired controlled thermal damage and depth of penetration at the frequencies listed above.

It is known that the depth of penetration of microwave energy inside biological tissue is a function of frequency and the dielectric properties of the tissue, hence in the instance where it is required to treat fine structures and cause a minimum amount of collateral damage, it is desirable to use microwave frequencies in the higher frequency bands (e.g. from the range given). On the other hand, where it is desirable to cause thermal damage to larger volumes of tissue, and the risk of damage to surrounding tissue does not outweigh the advantage of using point source thermal ablation, for example, for the treatment of large wounds, it may be desirable to use microwave frequencies in the lower frequency bands. In the instance where a high energy density, with a low depth of penetration is required to instantly raise the temperature of the tissue, for example to prevent excessive blood loss, it may be desirable to use high power and high frequency microwave energy, i.e. energy produced at the higher end of the band of frequencies deemed to be useful for implementation of the current invention. As an example, it may be desirable to produce 50 W of power at a frequency of 24 GHz.

The range of power levels considered as being useful for the implementation of the current invention is between 1.5 and 50 W. Where low power microwave power is required (low power is defined here as being less than 4 W) the DC power supply may be a battery contained with the microwave generator in the hand held unit. This may allow the whole apparatus to comprise a single portable unit.

Where higher power levels are required, it is desirable to use the two unit model discussed above, i.e. have the DC battery pack contained inside a separate unit with a DC cable used to connect the two units together. An advantage of this is to keep the weight of the hand held unit at a manageable level to allow the hand held unit to be manipulated with ease.

The battery or battery pack may comprise of disposable or a rechargeable batteries. Examples of battery technology that may be employed to implement the current invention are as follows: NiCd cells, Li polymer cells, Li ion cells, lead acid cells, alkaline cells and lithium tionyl chloride cells. The current invention is not limited to using these battery technologies. For example, a car or vehicle battery may supply DC energy to the portable system of the invention. The device may be plugged into the cigarette lighter in a car, or be attached to the battery of an ambulance, a tank, a fire engine or a police car using a suitable DC connector. This connector may be a customised connector. In the case of an ambulance, a +12 V DC supply will already be available to power other medical equipment used by paramedics or ambulance workers. If the unit is run from the battery of a vehicle, the start-up circuitry for the microwave power device (s) (and other sensitive microwave components) and the other control circuitry is preferably housed inside the hand-piece so that it can be powered from same single e.g. +12 V DC energy source.

It may be preferable to design the battery pack and control unit such that it will fit into a battery charger so that the unit can be recharged when not in use. It may be preferable to develop the system such that the hand-piece containing the microwave line-up can be attached (via a cable assembly containing the DC power delivery cables and any low frequency control signals) to the battery pack and control unit using a suitable DC connector to enable the microwave sub-assembly to be plugged into a number of pre-charged battery packs.

The battery pack may be attachable to the body of the user; the ability to wear the battery pack is of particular interest for treating war wounds and accident victims. When the unit is used in a doctor's surgery, hospital theatre, or a clinic, it may be permanently connected to a battery charger.

Preferably, a number of battery/control units are maintained on charge to enable the user to be able to always have access to a DC energy source for the unit. This is particularly advantageous when the device is used to treat medical procedures that may take a long time, e.g. 30 minutes or longer.

Preferably, the user interface includes a display indicating the treatment time available or treatment time left using the current battery pack. The means of indication may be a bar graph composed of a plurality of light emitting diodes (LEDs) or a small LCD screen display.

In another embodiment, the control electronics may be housed separately from both the battery and the hand held unit, i.e. the apparatus will comprise three units.

Preferably, the control unit includes a timing circuit arranged to effect correct order of operation of the components in the microwave generator. For example, where the microwave generator includes a transistor power device, the timing circuit may be arranged to ensure that the gate-source voltage to the power device is set to pinch off the channel between the drain and source to prevent current from flowing before the drain supply is connected and also that said gate-source voltage is applied to pinch off the channel before the drain voltage is removed. This arrangement is suitable when FET devices are used in the output power stage (power amplifier) of the microwave generator, wherein when the channel is open (or current can flow) the gate-source voltage is zero.

The control unit may also contain a means of controlling the level of microwave power produced by the microwave generator and a means of pulsing or modulating the microwave power produced at the output of the unit. For example, the control unit may control the modulation switch and attenuator unit discussed above. Adjustment of the level of microwave power produced, and the operation of pulsing the selected power level may also be implemented by varying the gate-source voltage applied to the FET devices used to form the output stage of the power amplifier (where MMIC devices are used, it may be possible to vary the DC supply voltage or one of the DC power supply voltages connected to the device).

Preferably, the control unit includes a sensing arrangement comprising analogue signal conditioning circuitry (e.g. analogue comparators and operational amplifiers) and glue logic (e.g. digital TTL, CMOS or ECL logic gates or counters) to process the signals produced by, the sensing elements discussed above. The processing functions performed may include taking the gate-source voltage to an appropriate level and then turning off the drain voltage supply in the instance whereby the reflected power level is excessive, driving a bar graph display to show the forward, and/or net delivered power level, driving LEDs that indicate microwave power is being delivered into tissue, and/or that the excessive reflected power has been detected, and/or a fault condition has occurred, and/or the device is armed and ready to deliver microwave power into tissue.

A switch may be provided to turn the drain supply on and off, i.e. to operate the system in pulsed mode. Pulsed mode operation may minimise device heating and reduce the possibility of the hand-piece heating up excessively. To implement this feature, the switch may cause a gate-source voltage necessary to cause the channel to be cut-off to be applied to the microwave power transistor (or to a plurality of microwave power transistors) used to form the output stage of the microwave power amplifier. Alternatively or additionally, all or part of the microwave generator may be mounted on a heatsink and/or suspended inside a plastic housing to minimize the risk of the hand held unit becoming excessively hot due to thermal conduction from the heatsink. As discussed in more detail below, a cooling system may be included in the hand held unit to transport heat away from the microwave generator.

The timing circuit may be arranged to switch the frequency source off before the drain supply when operating the system in pulsed mode to prevent the possibility of the frequency source turning the microwave power transistors on, i.e. the voltage generated by the frequency source signal provides a high enough gate-source voltage to cause a high level of drain current to flow.

The antenna in the microwave generator is preferably an elongate member adapted for delivering a microwave radiation field in a uniform manner to the biological tissue to be treated. The antenna may be a second aspect of the invention. Particularly suitable antenna structures may include suitably sized co-axial E-field needle (or monopole) antennas and H-field loop antennas. These antenna structures may have an overall diameter ranging from 0.5 mm to 10 mm, and lengths from less than 2 cm to greater than 12 cm. For example, the coaxial structures may have an outside diameter of between 0.5 mm and 2.2 mm and a length of between 2 cm and 4 cm. It is preferable for both outer conductor (jacket) and the inner conductor to be made from a hard metal to provide strength, for example, stainless steel. The outer surface of the inner conductor and the inner surface of the outer conductor may be coated with a highly conductive material, i.e. silver, in order to minimise conductor losses and associated structural heating.

Preferably, the antenna includes a dielectric tip at its distal end, which is adapted to function as the radiating end (aerial) and to create a matched condition between the co-axial antenna structure and the tissue to be treated. The dielectric tip may have a shape that is adapted for a particular use. The tip may be replaceable, e.g. to permit the same antenna structure to be used with different tips for different purposes. Electromagnetic field modelling tools, for example CST Microwave Studio® can be used to perform field simulations on suitable aerial (radome) structures in combination with biological tissue models that give dielectric information in terms of relative permittivity, loss tangent, and conductivity at the frequency of interest. The electromagnetic model may be combined with a thermal solver to provide information concerning the temperature distribution throughout the volume of tissue under consideration.

The antenna structures disclosed herein may be used to treat the medical applications listed above. The current invention draws on the use of relatively short co-axial treatment structures. A first structure comprises a co-axial cable with a ceramic tip that is made hemispherical to enable the distal tip to be rubbed over the surface of the tissue. The ceramic tip also acts as an impedance transformer to provide a static impedance match between the low permittivity dielectric material contained inside the co-axial cable and the high dielectric constant of the skin (or other biological tissue). A second structure, similar to the first, extends the diameter of the hemispherical radome to produce a larger radiating structure that may be used to treat larger tissue structures or to spread the energy over a larger surface area.

Larger antenna structures disclosed herein, e.g. comprising a plurality of needle antennas fed using an impedance transformer and terminating inside a hemispherical ceramic radiator, are particularly suitable for use with the high power version of the treatment system according to the first aspect discussed above. Such antennas may enable the invention to be used for treating wound injuries, for example, battle wounds or car accident wounds.

In one embodiment, a co-axial cable feed with a co-axial transformer is used to feed four radiating elements (monopoles) that are contained inside a hemispherical ceramic tip.

The antenna structure may be coated with a thin layer of biocompatible material that covers both conductors, but is transparent to the microwave energy. For example, a 10 μm thickness coating of Parylene C may be applied. This material may offer advantage in terms of preventing fluid or tissue ingress into the dielectric (entering at the interface between the ceramic tip and the outer jacket of the co-axial structure), and also allow the structure to be inserted into the tissue with relative ease. This may be advantageous where the device is to be inserted percutaneously, and minimally invasive procedures are to be performed. The ability to prevent fluid ingress is particularly advantageous when the system is used to measure tissue properties since ingress inside the dielectric between the inner and outer conductors of the co-axial cable can prevent useful magnitude/phase measurements to be made. Fluid or tissue ingress may also limit the efficiency of the tissue ablation process.

The dielectric tip may be sharpened, e.g. it may be a ceramic cone. The ceramic cone may act as an impedance transformer to provide a static impedance match between the coaxial cable and the tissue. The sharp (pointed) structure is useful for the treatment of thread veins or ligament tightening.

Preferably, the impedance of the apparatus is dynamically matched to the tissue being treated (e.g. as disclosed in WO 2004/047659 and WO 2005/115235). In the current invention, this can be advantageous because a tuning filter can be included in the microwave generator close the tissue treatment site. This means that the effects of insertion loss of a relatively long delivery cable between the microwave generator and the treatment antenna are eliminated.

The apparatus may include a reflected power monitor arranged to recognise certain behaviour in a reflected signal received back from the antenna and enable action to be taken automatically in response to the recognised behaviour. The behaviour in the signal may be indicative of a condition in the tissue being treated. For example, the signal may indicate that the impedance of the tissue is not changing, which may mean that the power delivered is insufficient for effective treatment. The power level may be increased automatically or manually in response to this recognised behaviour. In another example, this arrangement can be used to reduce or prevent the phenomenon or tissue 'spitting' that can occur during treatment. Tissue 'spitting' or 'popping' is thought to be caused by pressure building up where a energy emitting surgical instrument (e.g. probe) is inserted into tissue. The combination of pressure and energy from the instrument can cause small bits of tissue to be removed from the treatment site.

The behaviour of the reflected power can indicate in advance when a spit event is about to occur. It may be possible to prevent the spit event from occurring if suitable action is taken in response to the relevant behaviour.

Thus, the reflected power monitor may be arranged to detect a signature event in the reflected signals detected by the reflected radiation detector, and a power level adjuster may be connected between the source and antenna and arranged to automatically adjust a power level of the microwave radiation signal received by the antenna if the monitor detects a signature event.

The signature event may be any detectable behaviour in the reflected signal. For example, it may be a certain rate of change of reflected power or a constant level of reflected power for a certain time slot or duration. The signature event may be derived from behaviour in the reflected power, e.g. the reflected power may be used to determine changes in the impedance of the tissue; these changes may indicate the signature event. If the arrangement detects an event indicating that the antenna is held in one place for too long (e.g. a constant voltage indicative of a well matched condition is detected) then the power can be reduced to reduce or prevent collateral damage.

The reflected power monitor may be arranged to detect a rapid voltage spike in the reflected signal. For example, the monitor may include a differentiator arranged to measure a value of dv/dt (change of voltage with time) for the reflected signals. The differentiator may be arranged to compare the measured value to a threshold value, whereby the signature event is a value of dv/dt that is higher than a threshold. This arrangement may be used to detect tissue 'spitting', which the inventors have found is preceded by a voltage spike with a sharp rise or fall. The apparatus may continuously monitor the reflected power during treatment and if the signature event (value of dv/dt above the threshold) is detected, the power level may be arranged to immediately reduce the power level from a first value to a second value. Thus, the apparatus may back off (or reduce) the power level as soon as the signature (signal) that is known to lead to a 'spit' is observed. The first value of the power level may be one or more orders of magnitude greater than the second value of the power level.

The differentiator (e.g. slope detector differentiator) may be implemented in an analogue manner, i.e. using discrete operational amplifiers, signal comparators, an arrangement of capacitors and resistors and MOSFET switches, or using digital components, e.g. a computer or a DSP unit.

The threshold may be adjustable e.g. to enable a sensitivity to tissue spitting to be selected.

The power level adjuster may be arranged to ramp the power level back to the first value in a recovery time period after the reduction in power level. In practice, the power may need to be ramped back up relatively rapidly to permit treatment to continue without substantial instrument downtime or to ensure that the overall patient treatment time is not excessive. For usage in tumour ablation, it must be ensured that critical temperatures within the tissue are reached in order to ensure that all of the cancerous tissue/cells has/have been totally destroyed. The recovery time period may therefore be 100 ms or less.

The reflected radiation detector may be selected to be sensitive to the changes in the reflected signal which represent the monitored behaviour. Thus, if a diode detector is used e.g. connected to a coupled port of a directional coupler connected between the source and the antenna, then its rise/fall time may be selected to capture the signature event. For example, the detector may be a diode detector having a rise/fall time of 1 µs or less to capture the voltage spike associated with tissue spitting event that may exhibit a rise/fall time of 10 ms. In one embodiment, a tunnel diode based detector with a very fast pulse response may be used, e.g. product number ACTP1505N from Advanced Control Systems.

The power level adjuster may comprise an impedance adjustor connected between the source and the antenna. The impedance adjustor may also be used in an impedance matching arrangement, wherein the detector may be arranged to detect the magnitude and phase of the reflected signal and the impedance adjustor may have an adjustable complex impedance that is controllable based on the detected magnitude and phase. In this arrangement the impedance adjustor may therefore be arranged to match the impedance of the apparatus to the impedance of the load (tissue) to enable efficient power transfer. The impedance matching may be dynamic, e.g. adjustment may occur automatically in real time. When a signature event is detected by the monitor, the impedance matching may be overridden by the response to that signature event.

The reflected power monitor may also be arranged to provide user information e.g. to guide the surgeon during treatment. For example, the monitor may be arranged to emit an audible or visual signal when a signature event is detected. The audible or visual signal may be representative of the detected event. The audible signal may be any of a range of sounds or a digitally synthesised voice.

Preferably, the tuning filter contained within the hand held unit comprises one or more PIN diodes, varactor diodes or avalanche diodes, wherein a change in the voltage across the diode produces a change in phase or a phase shift of the microwave signal. For example, the operation of a varactor diode phase shifter relies on a change in the thickness of the depletion region of the diode to cause a change in the capacitance of the diode. This change in depletion layer thickness is brought about by applying a reverse bias voltage across the diode, i.e. the anode is made negative with respect to the cathode to increase the width of the depletion region to give a decrease in the capacitance. GaAs varactor diodes are preferred.

Alternatively, MEMS devices may also be used in the tuning filter. For example, a plurality of MEMS switches may be used to switch in and out an array of tuning elements in accordance with the value of the tissue impedance. A mechanical tuning stub arrangement using electromechanical actuators to move mechanical tuning rods (or screws) inside a suitable waveguide cavity is a possible alternative.

The tuning filter may comprise one or more tuning elements. Where an infinite range of tuning is required (all regions of the Smith chart can be accessed), the tuning filter desirably offers the same performance as a triple stub network where the distance between adjacent stubs is a quarter of the guide length at the frequency of interest. This functionality can be achieved using a variable series and a variable shunt element. For example, an open stub that can be varied in length between zero and a quarter wavelength at the frequency of interest, together with a means of moving the stub along a transmission line inserted between the load and the source by a distance of up to a half the wavelength at the frequency of interest will enable any load impedance to be matched to a fixed source impedance (e.g. nominally 50Ω). This tuning arrangement may be implemented using two varactor diodes, one connected in a series between the source and the load, and the other in shunt close to the load. In a preferred embodiment, the tuning arrangement uses a series connected adjustable coaxial trombone together with a shunt connected varactor (or avalanche or PIN) diode. The length of the coaxial trombone may be adjusted by means of an appropriate electromechanical adjuster to enable automatic phase adjustment to be performed. The width of the depletion region within the diode may be varied by applying a reverse biased voltage across the diode to enable automatic adjustment of the capacitive reactance of the second shunt connected tuning element. In theory, the capacitive reactance may be varied between 0Ω and ∞Ω, i.e. a movement from a short circuit to an open circuit on the Smith chart (or 0 to $\lambda/4$).

Other components of the system may also be implemented using MEMS technology. The use of MEMS devices in the system that incorporates dynamic tuning and/or tissue type/state measurements may be particularly advantageous due to the requirements for a small enclosure and the need to include a range of microwave components inside the hand-piece.

When dynamic impedance matching and/or tissue type and/or state recognition features are integrated into the hand held unit, a microprocessor, and/or a microcontroller, and/or a PIC device, and/or a digital signal processor (DSP) is/are desirably included in the system. Preferably this device (or these devices) are contained in the control unit to perform the necessary signal processing functions required to measure phase and/or magnitude information to make the necessary adjustments to the tuning filter to ensure that the microwave energy is being delivered efficiently into the biological tissue and/or to identify tissue type and/or state of the tissue from the signals measured impinging on the distal tip of the antenna. Where the tissue type and/or tissue state facility is required it is preferable to use a heterodyne receiver to enable phase and magnitude information to be made available; the signals from the output of the heterodyne receiver will be fed into the microprocessor (or other digital processing device). Information needed to determine tissue type and/or tissue state recognition may be provided by use of directional couplers or a microwave circulator. Where a microwave circulator is used, it is preferable for the forward and reflected power signals to be isolated from one another by at least 30 dB.

The microprocessor unit (and/or PIC and/or DSP) may also perform a power device start-up procedure (or sequencing) and sensing functions (i.e. as an alternative to analogue control circuits). Likewise, a small microprocessor or a PIC device may control the system even if dynamic tissue matching or tissue type and/or state measurements is not performed. For example, analogue comparators, operational amplifiers, counters and glue logic may be replaced by a single microprocessor or a PIC device.

Preferably, the user interface includes a display showing the level of forward power being delivered from the microwave source and/or the net power that is being delivered into the biological tissue being treated. Net power may be defined as the difference between the forward power from the output of the microwave source (power amplifier) and the reflected power coming back to the output port of the source (the output of the power amplifier). The means of indicating these power levels may be a bar graph composed of a plurality of light emitting diodes (LEDs) or a small LCD screen display.

A visible light source may be attached to the hand held unit to act as a means of illuminating the treatment area. The light source may further include a lens arrangement to focus a beam of light to a point at the distal end of the antenna structure where the microwave energy impinges onto the tissue. Desirably, the light source is arranged to produce a beam of light that is similar in 'shape' to the microwave field produced by the radiating antenna.

A third aspect of the current invention may be related to a cooling arrangement and a means of ensuring that the hand held unit remains cool.

As explained in more detail below, the current invention may be used to treat thread veins, to provide pain relief, to tighten muscle tissue, to seal off blood flow of wounded soldiers or car accident victims, to treat nasal polyps, and to treat ear, nose and throat (ENT) infections.

Thread veins are extremely common and sometimes embarrassing, mostly affecting the face and legs. The exact cause of thread veins are unknown although it is thought that they may be caused by changes in temperature, smoking, hormonal changes, alcohol and prolonged standing as well as being a possible inherited condition. Thread veins may be treated with the portable treatment system introduced here using very fine needle antennas.

A possible application of the current invention is also the removal of nasal polyps. Nasal polyps block the nose and large polyps can prevent nasal breathing, forcing the individual to breathe through their mouth. They also cause reduced sense of smell. Occasionally, they swell so much that they emerge from the nostril.

Polyps are caused by the soft tissue lining of the sinuses becoming swollen, and filling the available space, which can expand into the nose forming a growth known as a polyp. As there are a number of small sinuses between the eye and the nose, when polyps do occur, there will usually be several of them. The most effective treatment for nasal blockage due to polyps is surgical removal. The current invention maybe used with a radiating loop antenna to treat this condition.

The current invention may also be used to tighten muscle ligaments, for example, in the leg or the eye. Again, small needle antenna structures may lend themselves particularly well for use in these applications. The higher power version of the portable unit maybe used where it is necessary to use key hole surgery to access the ligaments.

The invention may also be used to ablate nerve endings for the purpose of pain relief, for example, the ablation of nerve plexi. This particular application may relate to palliative care for patients suffering from cancer to reduce suffering and may provide an alternative to morphine or pain killers. The invention may also be used to treat conditions relating to the back and neck where intervertebral discs have been damaged.

The potential applications of the current invention are not limited to those listed above. The system may be used to treat other conditions, e.g. treatment of breast tumours, treatment of prostate cancer, treatment of kidney tumours, treatment of brain tumours, the treatment of liver tumours, and biological tissue resection.

BRIEF DESCRIPTION OF THE DRAWINGS

Embodiments of the invention are discussed below with reference to the accompanying drawings, in which.

DETAILED DESCRIPTION; FURTHER OPTIONS AND PREFERENCES

Figure 1:
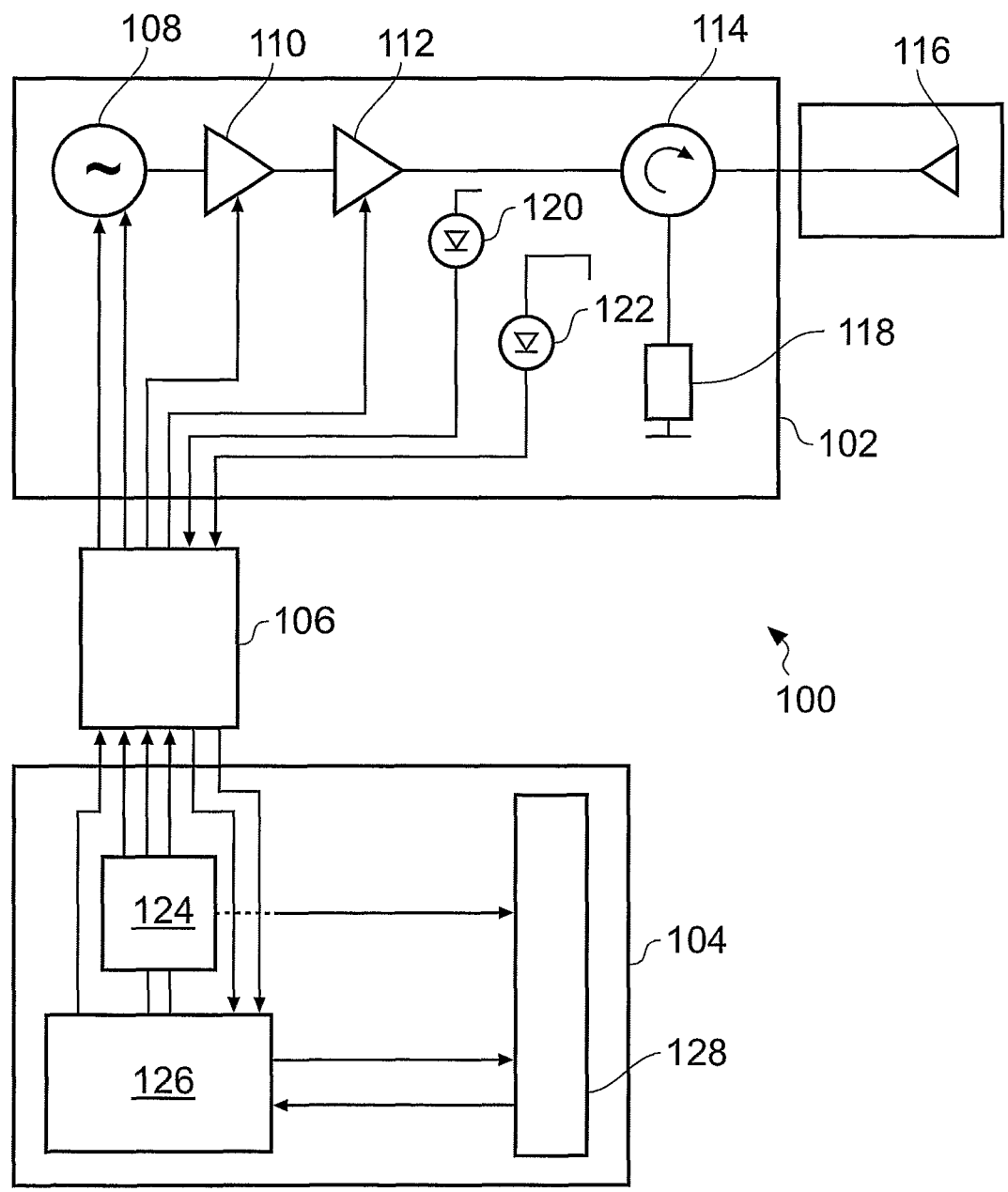
FIG. 1 is a block diagram showing an electrosurgical ablation/cauterisation system that is an embodiment of the invention.

FIG. 1 shows an, overall diagram of a portable electrosurgical system 100 that is an embodiment of the invention. The system is split into two sub-systems 102, 104 and the two units are connected together using a flexible cable assembly 106, e.g. comprising DC power supply cables and low frequency signal control lines. This arrangement offers advantages over using long sections of microwave signal carrying cable in terms of not losing expensive microwave power through power loss along the cable and also overcoming potential limitations relating to phase variation and magnitude variation with flexure that may be associated with long lengths of microwave cable. This arrangement may also overcome undesirable effects associated with temperature variations along the cable assembly, for example, cable heating and variation in phase/magnitude. The two sub-systems are now discussed in detail.

The first sub-system is a hand-held (portable) microwave sub-assembly 102. Microwave sub-assembly 102 contains a frequency source 108 that is used to generate a low power signal at a predetermined frequency, a driver amplifier 110 to amplify the output signal level produced by the frequency source, and a power amplifier 112 to amplify the signal produced by the first amplifier to a level that may cause controlled tissue destruction. The output from the power amplifier 112 is connected to a microwave circulator 114 which is used to protect the output of power amplifier 112 from excessive amounts of reflected power caused by an impedance mismatch at the distal end of the treatment antenna 116. The circulator 114 only allows microwave power to flow in a clockwise direction, hence any reflected power coming back into power amplifier 112 will be absorbed by power dump load 118. In the instance where low output power levels are being generated, for example 1.5 W continuous wave, it may be possible to omit the microwave circulator and the 50Ω power dump load from the design whilst maintaining the device operability (the worst case level of reflected power is such that damage will not be caused to the output stage of the power amplifier). Forward and reflected power levels are detected using diode detectors 120, 122 to measure a portion of the forward and reflected power respectively. The microwave power may be sampled using either directional couplers or E-field probes inserted into the first (forward) and third (reflected) port of microwave circulator 114. The signals produced at the output ports of diode detectors 120, 122 enable levels of forward and reflected power to be measured and from this information it is possible to calculate the net power delivered into the tissue (forward power—reflected power) and switch off the power amplifier 112 (and/or driver amplifier 110) if the level of reflected power exceeds a predetermined threshold. For applications where power levels of less than 1 W to around 3 W are used to treat small tissue structures or cause tissue necrosis to a small volume of tissue, i.e. produce a spherical coagulation with a diameter of less than 5 mm, it may only be necessary to use the driver amplifier 110. A MMIC amplifier may be used in this instance. Suitable candidates for the frequency source 108 include voltage controlled oscillators (VCOs), dielectric resonator oscillators (DROs) or Gunn diode oscillators. For example, an MMIC VCO from Hittite Microwave Corporation (product number: HMC531 LP5/531 LP5E) is particularly suitable. For the driver amplifier, and HEMT MMIC transistors from TriQuint semiconductor (e.g. product numbers: TGA2904-EPU-FL, TGA8658-EPU-SG, TGA2902-SCC-SG, TGA8659-EPU-SG or TGA2502-EPU) are suitable. Likewise, a HEMT MMIC transistor may be used for the power amplifier (e.g. product numbers: TGA2514-EPU & -FL). However, GaAs FET power devices are also suitable (e.g. TGA2924-EPU-SM, TGF2021-XX or TGF1034-24-EPU from TriQuint Semiconductor, or TIM1414-8-252 or TIM1414-18L-252 from Toshiba Microwave).

The above-mentioned transistors may be operated in pulsed mode, where the DC power supply or drain voltage is switched off if the microwave output power is zero. Pulsed mode operation is preferable where power levels in excess of a few watts are required since this ensures the temperature of the hand held unit which contains microwave sub-assembly 102 is not excessive or does not cause any discomfort to the user. New technology devices that enable microwave power to DC power efficiencies in excess of 50% may also be considered to alleviate or ameliorate problems associated with DC heating of the hand-held device.

For implementation of the pulsed mode of operation, a control unit 104 is used to ensure that the microwave power generating devices 108, 110, 112 are switched on and turned off in a particular sequence to ensure that device damage does not occur when the unit is operated in this mode. This can be particularly important when using discrete devices since it is desirable for the channel to be cut off (i.e. current flowing between the drain and source is close to zero) by application of an appropriate gate-source voltage before the drain voltage is connected. For the turn-off procedure it is desirable for the channel to be cut-off by application of an appropriate gate-source voltage before the drain voltage is removed.

The second sub-system comprises a control unit 104 containing a battery pack 124 with a start-up circuit (not shown) for supplying power for GaAs FET device operation and sequencing, a control circuit 126 and a user interface 128. It may be desirable for the start-up circuit to be an integral part of the control circuit 126. It may be preferable for the control circuit 126 to take the form of a small microprocessor or a PIC device or it may comprise analogue comparators and operational amplifiers, and digital logic devices (glue logic and counters). The user interface 128 may be a combination of any of LED bar graphs, single LEDs and switches, an LCD alphanumeric display and switches (micro switches or membrane switches) or a small touch screen display. The battery pack may be a single or plurality of disposable cells or a single or plurality of rechargeable cells. The control unit 104 may also contain a recharging unit or be arranged to accept a standard mains charger, for example a mobile phone charger unit.

The two sub-systems 102, 104 are connected together using a single or a plurality of DC feed cables and a plurality of low frequency signal cables. The latter may be thin co-axial assemblies that are suitable to carry signals up to frequencies of 100 MHz. The DC feed cables and the low frequency signal cables may be contained within a single jacket. It is preferable to use a flexible material to implement said jacket. A flexible rubber may be most suitable, for example, neoprene rubber.

A suitable antenna 116 is connected to the output of the microwave sub-assembly 102. The antenna 116 can be removable, e.g. to enable a variety of antenna structures to be connected to the output of the device. The antenna 116 is connected via a microwave connector (not shown), e.g. SMA, SMB and MCX. A push fit connector is preferred to mitigate the risk of cross threading or over tightening.

Figure 2:
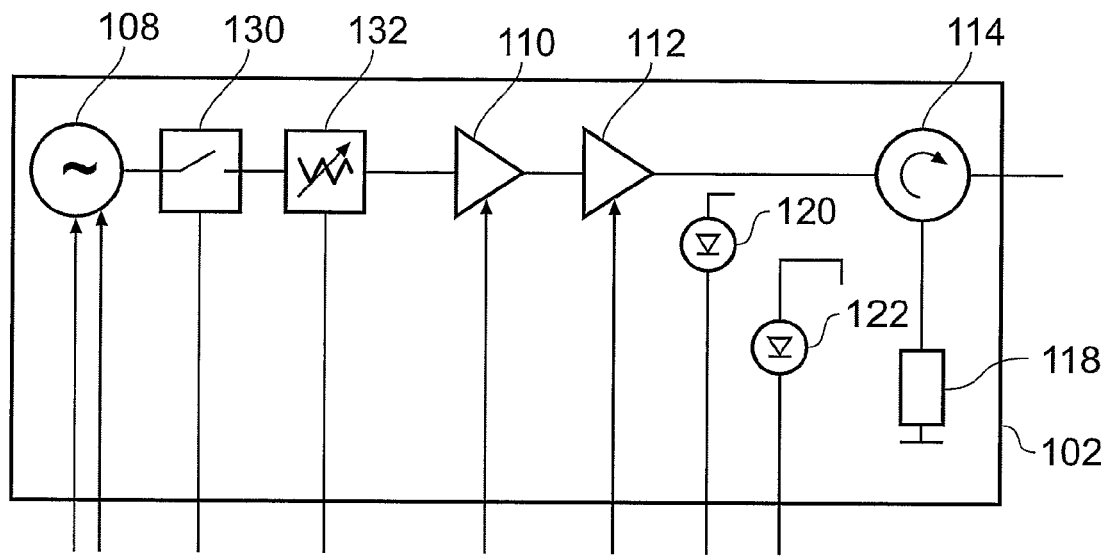
FIG. 2 is a block diagram showing a microwave line-up for an electrosurgical ablation/cauterisation system that is another embodiment of the invention.

FIG. 2 shows the microwave sub-assembly 102 of FIG. 1 with two additional microwave components. A modulation switch 130 is included to enable the hand-held electrosurgical system to be operated in a pulsed mode. This mode of operation is particularly useful when the unit is operated at higher microwave power levels, for example, 15 W to 50 W, where thermal effects relating to the hand-piece must be considered. FIG. 2 also shows a power control attenuator 132, which is used to enable the user to control the level of power delivered into the tissue. Again, it may be desirable to include this feature where the unit is configured to be capable of delivering power levels up to, and possibly in excess of, 50 W. MEM technology can be used to implement the modulation switch 130 and power control attenuator 132. Source oscillator 108 may also take advantage of MEM technology to help miniaturise the overall size of the hand-piece.

This invention is not limited to using a separate (or external) modulation switch and/or power control attenuator unit; these features (or operations) may be implemented by varying the level of voltage applied to the power generating devices. The variation of gain due to variation in DC or bias voltage may be around 15 dB. If wider variation is desired, a digital attenuator comprising of a bank of PIN diodes can be used. This may provide a variation of gain of up to (and in some cases in excess of) 64 dB.

Figure 3:
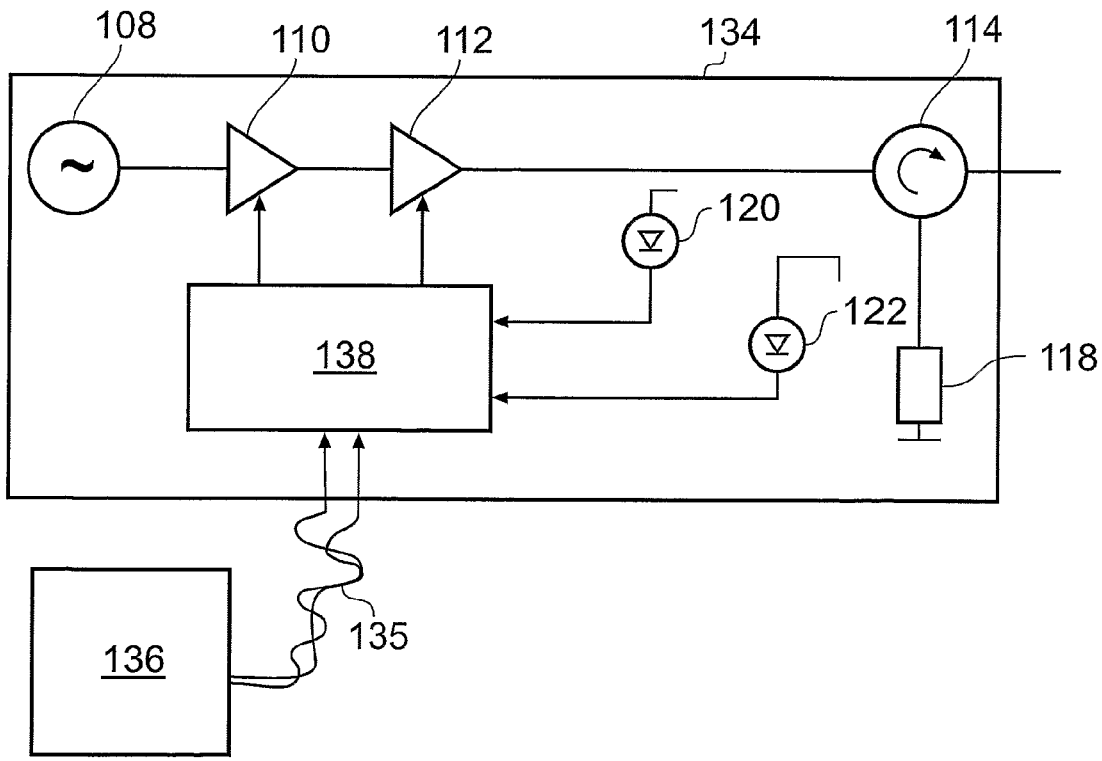
FIG. 3 is a block diagram showing a portable electrosurgical system connected to a battery that is another embodiment of the invention.

FIG. 3 shows an embodiment of a hand-held device 134 connected via flexible power leads 135 to a battery 136, e.g. a car battery, an ambulance battery, a fire engine battery or a tank battery. The hand-held device 134 includes the microwave line up from the microwave sub-assembly 102 in FIG. 1. Additionally, the hand-held unit 134 includes the start-up and control circuitry 138 (e.g. includes the control circuit 128 mentioned above). In this embodiment, it may be desirable to implement the control electronics using analogue devices since it may be beneficial to limit the functionality of the overall system. A small low power PIC could also be considered to implement the start-up and control functions for this embodiment.

Figure 4:
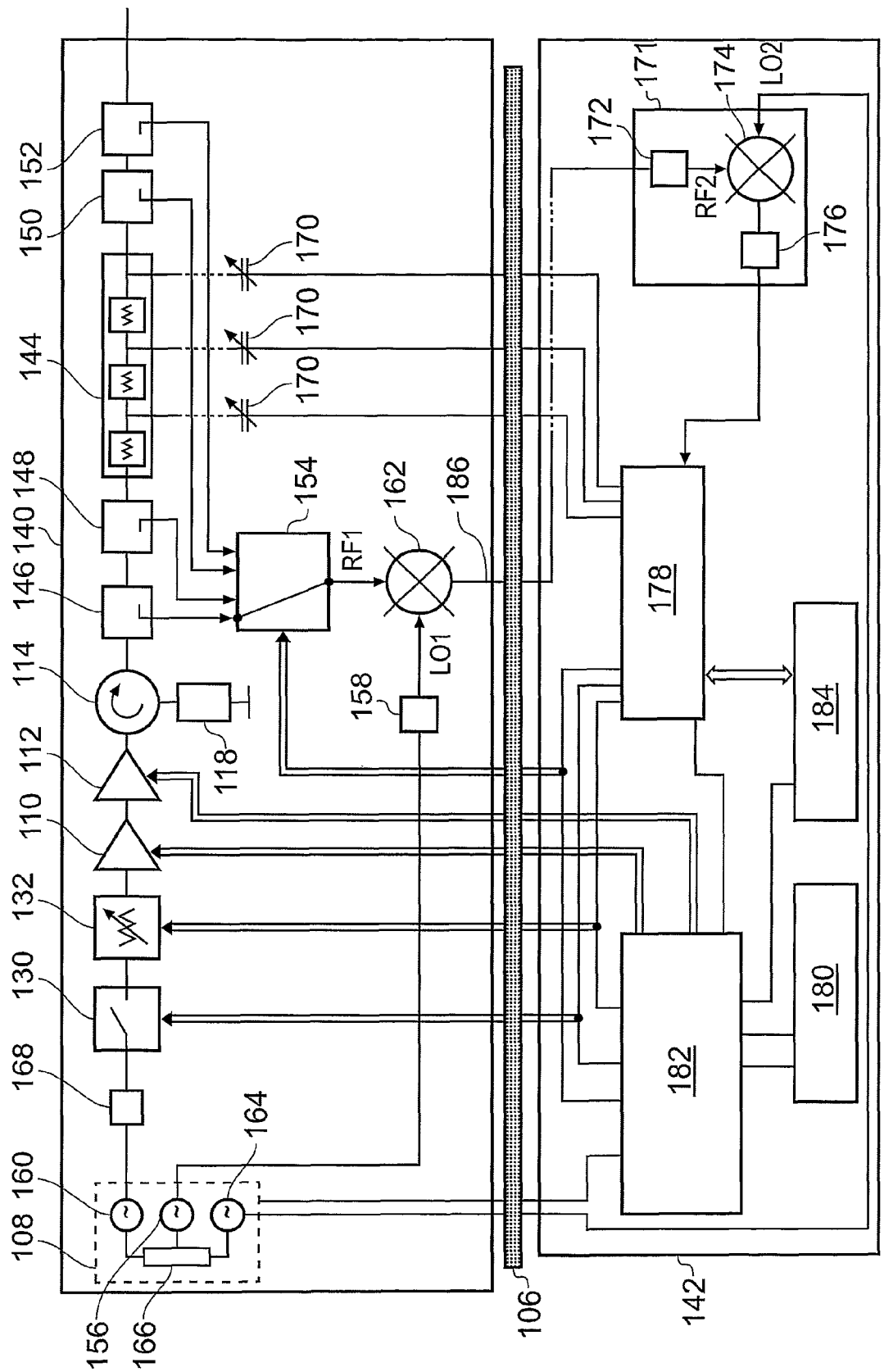
FIG. 4 is a block diagram showing the internal components of an electrosurgical system configured to perform dynamic impedance matching that is another embodiment of the invention.

FIG. 4 shows another embodiment of the system of the present invention. This embodiment uses a dynamic impedance matching system to enable the microwave energy developed by the power amplifiers 110, 112 to be matched, in terms of impedance, with the load presented to the distal end of the radiating antenna (not shown) by the state of the biological tissue. It may be preferable for a conjugate match to be performed. This configuration offers advantage in terms of efficient energy delivery into tissue, reduced treatment time, and the ability to accurately quantify energy dosage required to cause controlled tissue destruction due to the fact that the demanded power is the power that actually gets delivered into the tissue due to the fact that the matching algorithm prevents the occurrence of reflected power. The system shown in FIG. 4 resembles the system of FIG. 1 and like components have the same reference number accordingly. Broadly, the system comprises a hand-held unit 140 connected via cable assembly 106 to control unit 142. Additional microwave circuitry is contained within the hand-held unit 140. The additional microwave circuitry includes a tuning filter 144, four directional couplers 146, 148, 150, 152, a time multiplexing switch 154, and the first stage of a double IF heterodyne receiver that comprises a first local oscillator 156, a band-pass filter 158 used to remove any signal components of the primary frequency source 150, and a microwave frequency mixer 162. Other components contained within the hand-piece which enable the dynamic impedance matching system to be implemented are a third frequency source 164 to provide a local oscillator signal for the second stage of the double IF heterodyne receiver (contained in the control unit 142), a reference frequency oscillator 166 to enable the three signal oscillators 156, 160, 164 to be synchronized together, and a second band-pass filter 168 connected between the output of the primary frequency source 160 and the input to modulation switch 130 to remove any signal components that may be present at the frequency of the first local oscillator signal 156.

In this arrangement, the time multiplexing switch 154 is used to enable signals from any one of the four coupled ports of reflected signal couplers 146, 148, 150, 152 to be channelled into a double IF frequency down converter circuit (at mixer 162) to enable phase and magnitude extraction to be performed. It may be necessary to compare the information available at the later coupled ports 150, 152 or the earlier coupled ports 146, 148 to determine the adjustments required to the tuning elements 170 within (or outside) tuning filter 144 to enable the power source (i.e. power generated by amplifier 110 or a series connected chain of amplifiers 110, 112) to be impedance matched with the tissue load. As shown, adjustment may be implemented by adjusting the voltages on three diodes. The tuner 144 may take the form of a plurality of tuning stubs contained within a tuning cavity, where an electromechanical actuator is used to move said tuning stubs within the cavity, and a controller, for example a PID controller, is used to ensure that the movement of the tuning stubs (rods) is well defined. A number of topologies may be considered for the implementation of tuning filter 144, but to enable a compact hand-held system to be realized, it may be preferable to use an arrangement of PIN or varactor diodes.

The operation of microwave frequency mixer 162 is to enable a portion of the high frequency microwave signal that is used to cause controlled tissue damage to be mixed down in frequency to a signal at a lower frequency, whilst preserving phase and magnitude information available from the coupled ports of the four directional couplers 146, 148, 150, 152. The desired output frequency from mixer 162 is the difference frequency between a first input RF1 from the couplers and a second input LO1 from the local oscillator 156. In the configuration given in FIG. 4, the difference between the RF1 input and the LO1 input is 50 MHz because the local oscillator 156 operates at 14.45 GHz while the primary frequency (to which the couplers are coupled) is 14.5 GHz. The 50 MHz signal is used to extract phase and magnitude information. This invention is not limited to using the arrangement shown that uses four directional couplers (146, 148, 150, 152). For example, the latter two (150, 152) only may be used, or the former two (146, 148) only may be used.

MEM technology is desirable to implement as many of the microwave devices contained within the line-up shown in the hand-held unit 140 in order to ensure that the unit is as small and lightweight as possible.

The control unit 142 in FIG. 4 contains the second stage of the double IF heterodyne receiver used to extract phase and magnitude information that is used to control the adjustable elements contained within tuning filter 144. The second stage 171 of the double IF heterodyne receiver comprises a third band-pass filter 172 used to remove signals other than the difference IF signal produced at the output of first mixer 162, second mixer 174 used to mix the frequency down yet again to a value that can easily be dealt with using a standard analogue to digital device, and a fourth band-pass filter 176 used to remove all signal components present at this point in the system at frequencies other than the difference IF signal produced at the output of second mixer 174. In this embodiment, the mixer produces the difference between a first input RF2 from the first mixer 162 and a second input LO2 from the third frequency source 164. In this embodiment, the third frequency source operates at 40 MHz, so the difference is 10 MHz. The output from fourth band-pass filter 176 is fed into a digital processor 178, which may be a digital signal processor, a microprocessor, or a microcontroller, to enable the phase and magnitude information to be converted into a format that can be used to control the variable elements within the tuning filter 144 based on the information measured at the coupled ports of directional couplers 146, 148, 150, 152 (or a combination of) and directed to the heterodyne receiver using multiplexing switch 154. It may only be required to use information available at the coupled ports of later directional couplers 150, 152 to control the variable tuning elements used to maintain the matched condition.

Battery pack 180 provides the required DC energy for the electrosurgical unit to operate. The battery pack 180 may comprise disposable cells or rechargeable cells. A voltage control unit 182 may comprise a plurality of DC to DC converters to enable a single voltage produced by battery pack 180 to be converted to a plurality of voltages necessary to operate the unit, for example, the drain and gate-source voltages for power GaAs devices, the voltage to power up the microprocessor unit, etc. The voltage supplies and control signals are shown in detail in FIG. 5, discussed below. The DC to DC converters may take the form of a buck and boost converters or DC regulators. It may be preferable to tap off the voltage produced by a number of series connected cells that are used to form the battery pack rather than using DC to DC converters, for example, a battery pack comprising of four 1.5V cells will provide 1.5V, 3V, 4.5V and 6V rails. The advantage of using this method is that noise generated by the switching process used to implement buck and boost converters is eliminated and there is no power conversion loss.

The selection of the pole position of single-pole-four-throw (SP4T) time multiplexing switch 154, the open/close operation of modulation switch 130, and the level of attenuation introduced by variable attenuator 132 are determined by control signals generated by microprocessor 178.

User interface 184 may take the form of LED bar graphs, single LEDs and micro-switches, or an alphanumeric LCD display with micro-switches or membrane switches, or a miniature touch screen display.

The two units 140, 142 are connected together using a cable assembly 106 that contains the DC power supply cables and low frequency signal cables. For the implementation shown in FIG. 4, it is desirable to use a co-axial line 186 to send the 50 MHz IF signal from the output port of first frequency mixer 162 contained within the first unit 140 (hand-held unit) to the input port of third band-pass filter 172 contained within the second unit 142. The co-axial cable used may be thin cable and does not need to comprise of high performance dielectric material. It may be preferable to house the second stage 171 of the double IF heterodyne receiver within the first unit 140 in order to further reduce the performance requirements for the transmission lines between the two units. Also, a one stage heterodyne receiver could be used in order to reduce the complexity of the system.

Figure 5:
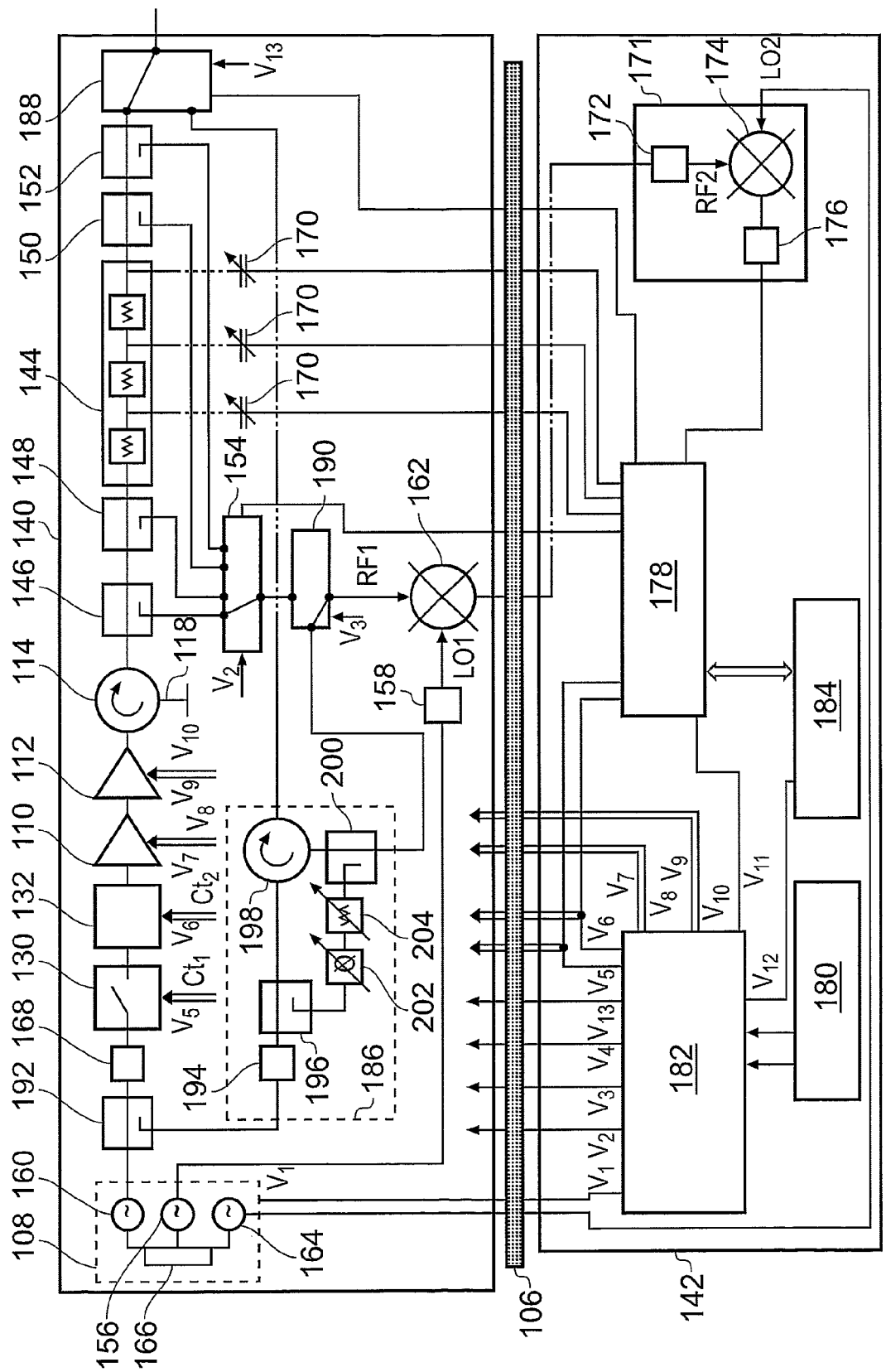
FIG. 5 is a block diagram showing the internal components of a dual channel dynamic impedance matching electrosurgical system that is another embodiment of the invention.

FIG. 5 shows another embodiment of the invention where both dynamic impedance matching and tissue type/state recognition is performed. In this configuration, a low power transmitter 186 is included in the first unit to provide a separate tissue measurement (dielectric) channel that can be used to identify various anatomical structures as the antenna is pushed into or placed on top of biological tissue. In this embodiment, a waveguide switch 188 and a co-axial switch 190 are used to enable switching between the two channels of operation, namely the high power controlled ablation mode and the low power tissue measurement mode. The control signals to enable the switch position of waveguide switch 188 and co-axial switch 190 to be changed over is provided by microprocessor 178 contained within the control unit 142. This invention is not limited to using a waveguide switch and a co-axial switch to switch between the two modes of operation; for example, it may be possible to use two co-axial switches, two waveguide switches, a combination of PIN and waveguide switches, or a combination of PIN and co-axial switches. The low power transmitter 186 contained within the hand-piece unit 140 is fed from a directional forward coupler 192 used to sample a portion of the signal generated by primary frequency source 160, i.e. the signal at the measurement frequency. The coupled signal is fed into the input port of a band-pass filter 194 whose function is to pass energy produced at the measurement frequency, but reject energy produced at all other frequencies. The output from filter 194 is fed into the input of first directional coupler 196, which is configured as a forward power directional coupler and forms a part of a carrier cancellation circuit. The output from first directional coupler 196 is fed into the first port (the input port) of microwave circulator 198. The second port of circulator 198 is connected to the measurement antenna via waveguide switch 188. The third port of microwave circulator 198 is connected to the input to second directional coupler 200, which is configured as a forward power directional coupler and forms a part of a carrier cancellation circuit. The output from second directional coupler 200 is fed as RF input to first frequency mixer 162 via co-axial switch 190 of the double IF heterodyne receiver.

The configuration and description of the double IF heterodyne receiver is similar to that given in FIG. 4. In the measurement mode, the phase and magnitude information is extracted from the signal and processed using microprocessor 178 to provide information relating to the tissue type and/or the state of the tissue that the distal tip of the antenna is making contact with.

To enhance the isolation between the forward transmitted signal and the reflected signal in the measurement mode it is necessary to provide a high a level of isolation between the first and third ports of circulator 198. Preferably, the circulator 198 is tuned or optimized at the measurement frequency for low insertion loss in the signal path and high rejection in the isolated path. Additional isolation may be provided by means of a carrier cancellation circuit comprising first forward directional coupler 196, phase adjuster 202, adjustable attenuator 204, and second forward coupler 200. The carrier cancellation circuit works by taking portion of the transmit signal from the coupled port of coupler 196 and adjusting the phase and power level such that it is 180° out of phase out of phase and of the same amplitude as any unwanted signal that gets through to the third port of circulator 198 to enable the unwanted signal component to be cancelled out. The carrier cancellation signal is injected into the output of the third port of circulator 198 using second forward coupler 200. The carrier cancellation circuit may also be used to adjust for variations caused by the output antenna (co-axial shaft and probe tip).

All other elements of the configuration shown in FIG. 5 are described in detail in the description relating to FIG. 4 given above.

The measurement channel may use the same components as the ablation channel. In other words, this invention is not limited to using two separate channels for implementing the measurement and ablation channels. Thus the low power circuit described above may be omitted.

Other microwave components may be provided in the system to provide enhanced measurement sensitivity and protection, for example, low noise signal amplifiers, driver amplifiers, signal isolators, attenuator pads, and additional signal filters. These components are not shown here, but a person experienced in the art of microwave engineering would be aware of the configuration.

In order for the system to be able to recognize tissue types and/or tissue states, it will be necessary to calibrate the antenna. Calibration may be performed by connecting a load, or a plurality of loads, to the distal tip of the antenna to provide a known reference point (or a plurality of known reference points).

In a further embodiment, the hand-held device may only provide the tissue type and/or state measurement function. In this embodiment, the following microwave components of the embodiment in FIG. 5 are not essential: directional coupler 192, band-pass filter 168, modulation switch 130, gain controller 132, amplifiers 110, 112, circulator 114, directional couplers 146, 148, 150, 152, tuning filter 144, waveguide switch 188, time multiplexing switch 154, and co-axial switch 190. The device configured for measurement use only may be used to identify various tissue types or to identify the stage of a particular disease or illness. The advantage of this embodiment of the dielectric measurement device is that the microwave transceiver electronics is positioned close to the distal tip of the measurement antenna, which will reduce or eliminate variations in phase and magnitude information due to cable bending, flexing, twisting or crushing that may occur in a system where the measurement electronics (the microwave transceiver 186) is positioned in isolation with respect to the measurement site (or the distal tip of the measurement antenna). This feature may increase the measurement sensitivity of the system. An arrangement that comprises of low power microwave electronic components to form a microwave transceiver similar to the one shown in FIG. 5 could be physically integrated into a very small package by making use of micro-electromechanical systems (MEMS) technology.

Figure 6:
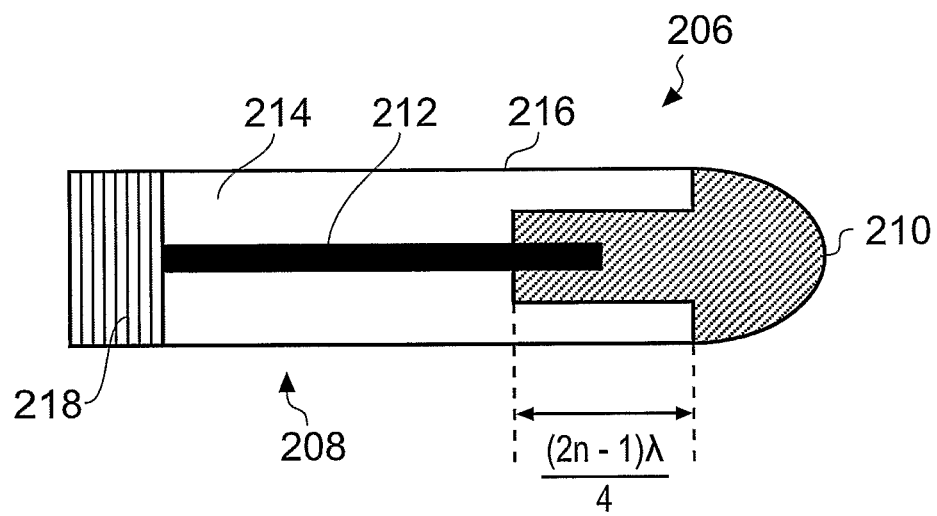
FIG. 6 is a cross-section through a treatment antenna with hemispherical tip that is suitable for use in an embodiment of the invention.

FIG. 6 shows a first antenna structure that may be an embodiment of the invention. The antenna 206 comprises a body 208 made from a rigid section of co-axial cable, with a hemispherical radiating tip 210 attached to the distal end. The co-axial cable is fed with power via a microwave connector 218. The body 208 has a central conductor 212, e.g. of copper, surrounded by a dielectric material 214 (e.g. air or PTFE or Teflon which is held in an outer jacket 216 (e.g. of stainless steel). The tip 210 can be made from a hard microwave ceramic. The tip 210 may also perform the function of an impedance transformer to enable the impedance of the co-axial cable 208 to be matched to the impedance of the treatment tissue. It may be preferable for the impedance matching transformer to be a quarter wave transformer consisting of length equal to an odd multiple of a quarter of the wavelength at the frequency of interest and an impedance equal to the square root of the product of the characteristic impedance of the cable 208 and the impedance of the tissue. The hemispherical tip may lend itself well in applications where it is desirable to rub the applicator onto the tissue or over the surface of the tissue, i.e. it is undesirable to insert the applicator inside the tissue.

Figure 7:
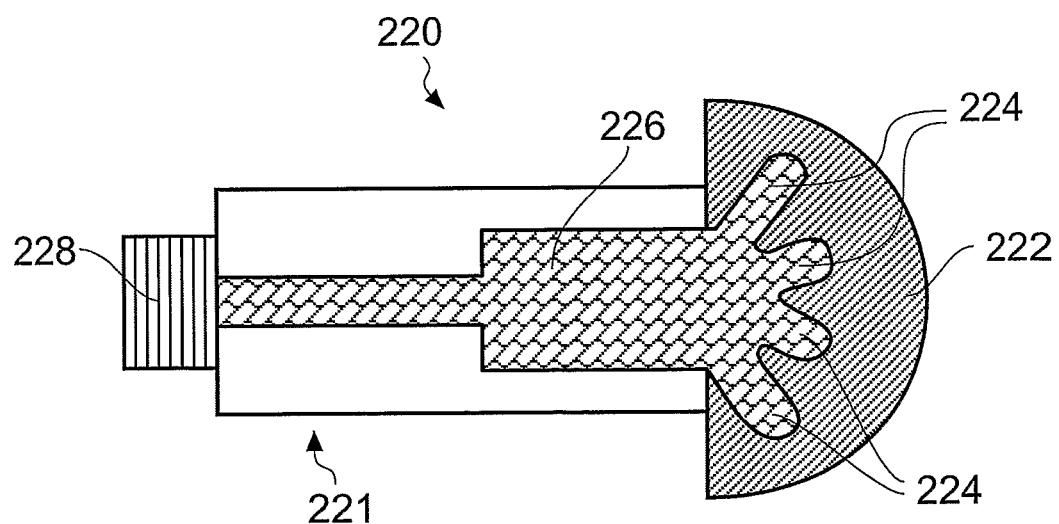
FIG. 7 is a cross-section through a treatment antenna with an enlarged tip that is suitable for use in an embodiment of the invention.

FIG. 7 shows another antenna structure. This antenna 220 has a co-axial body 221 with a large hemispherical radiating head 222 fed using four monopole radiating elements 224 to enable the microwave energy to be evenly distributed. A quarter wave co-axial transformer 226 is used to provide a good impedance match between the co-axial body 221, which has an impedance of 50Ω, and the four radiating monopoles 224 fitted inside the hemispherical tip. It is preferable for the tip to be made from a low loss microwave ceramic material. This antenna structure may be used to treat larger lesions, or be used at power levels that are defined here as being high, for example, 20 W to 50 W to be used as a wound sealing device to treat battle field injuries or accident victims, where it may be required to instantly stop blood flow from a gaping wound. The antenna shown here may use 6.35 mm outside diameter rigid co-axial cable terminated at the proximal end with a suitable SMA connector 228. A suitable cable may be type HC-12009-1 low loss aluminium 6.35 mm cable from Haverhill Cable and Manufacturing Corporation with an attenuation of 21 dB/100 ft. and an average power rating of 700 W at 10 GHz.

Figure 8A:
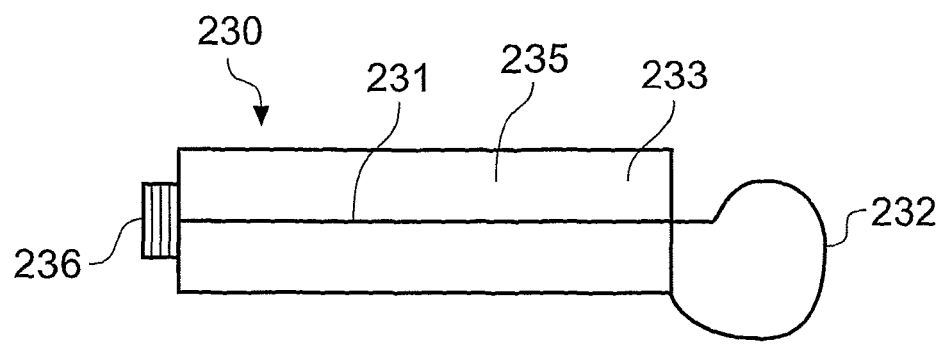
FIGS. 8(*a*) and 8(*b*) show cross-sections through treatment antennas having, respectively, an H-field loop antenna and monopole antenna that are suitable for use in an embodiment of the invention.
Figure 8B:
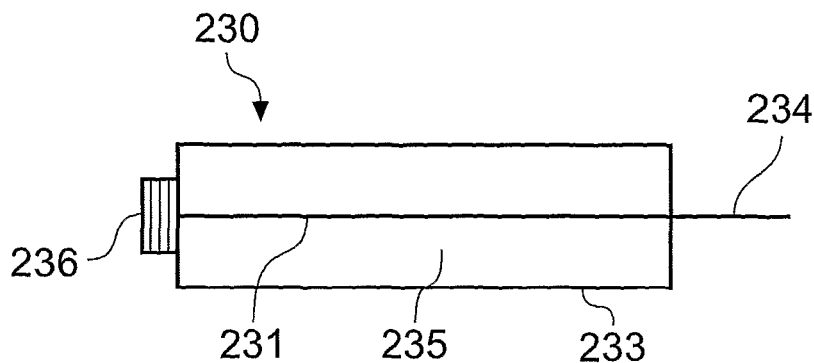

FIGS. 8(a) and 8(b) show further antenna structures that may be embodiments of the invention. Each structure comprises a co-axial body 230 having an inner conductor 231 separated from an outer conductor 233 by a dielectric material 235. The co-axial body has a microwave connector 236 at an end proximal to the power source (not shown).

FIG. 8(a) shows a radiating loop antenna 232 connected at the distal end of the co-axial body 230. This structure may be used to treat small surface lesions or nasal polyps. FIG. 8(b) shows a radiating monopole antenna 234 at the distal end of the coaxial body 230. This structure may be used to treat individual thread veins or could be useful in certain ear/nose/throat (ENT) procedures, where access is limited and small antenna structures are of interest.

The structures shown in FIGS. 8(a) and 8(b) are particularly well suited for use with a 2.5 W electrosurgical system that is a specific embodiment of the current invention. The outside diameter of the antenna structures considered here is between 0.5 mm and 2.2 mm. The overall lengths of the antenna structures ranged from 1.5 cm to 6.0 cm.

Suitable products for the co-axial cable 230 include: HC 60004-1; HC 10009-1; and HC 20000-1: from Haverhill Cable and Manufacturing Corporation (www.haverhillcable.com). The shape of the radiating antennas can be determined using suitable electromagnetic field simulation tools (e.g. CST Microwave Studio) and a suitable vector network analyser (e.g. Agilent 8720ET unit).

Figure 9:
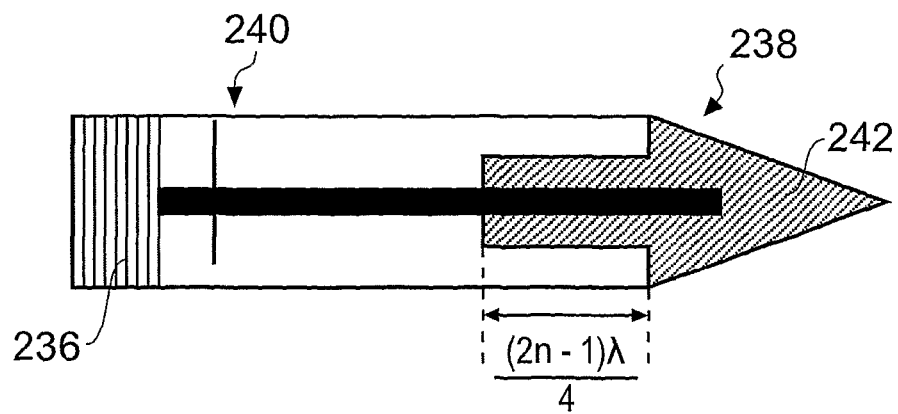
FIG. 9 shows a cross-section through a treatment antenna with a sharpened tip that is suitable for use in an embodiment of the invention.

FIG. 9 shows a further antenna structure that may be used with the current invention. This antenna 238 consists of a co-axial feed cable 240 similar to co-axial body 230 described above, and a pointed ceramic dielectric tip radiating antenna 242. The radiating antenna section 242 may also enable impedance matching to be performed between the co-axial feed cable assembly and the tissue that forms the load impedance. This antenna structure may be used to treat single (or very small clusters of) thread veins, to tighten ligaments (cartilage or eye muscles), or be used in pain relief applications (ablating nerve plexi) where the antenna may be inserted percutaneously into various tissue structures within the body. Due to the possible need to insert this antenna structure through the skin to treat tissue that may be several centimetres away from the surface of the skin, it may be desirable for output power levels of up to 30 W to be generated, and for the overall length of the antenna to be in excess of 10 cm.

Figure 10:
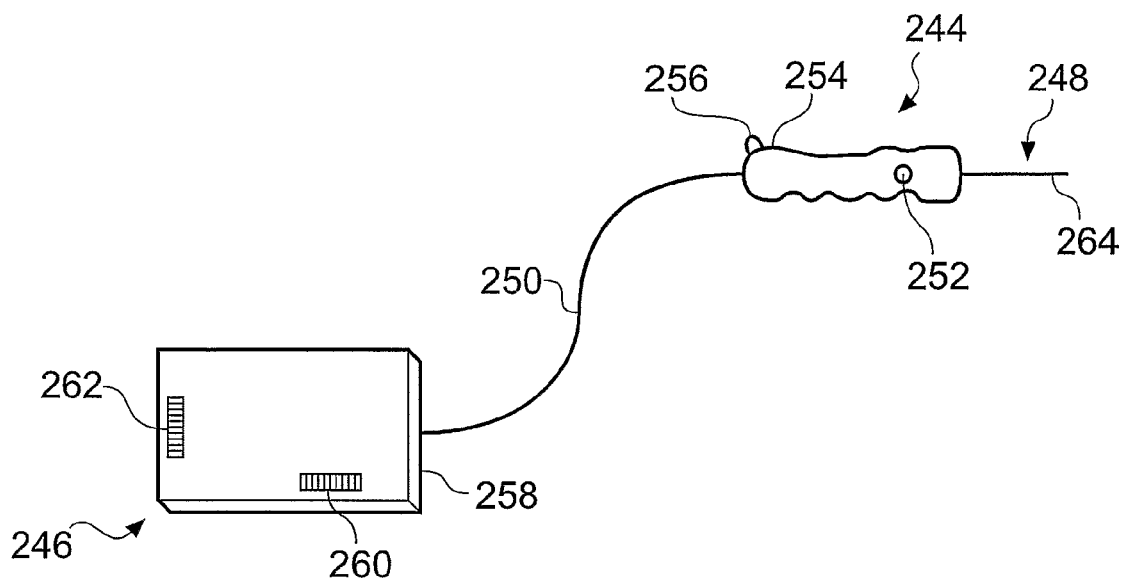
FIG. 10 shows a schematic drawing of an electrosurgical system that is another embodiment of the invention.

FIG. 10 shows a schematic drawing of another embodiment of the complete hand-held electrosurgical instrument. The system comprises four main components. Firstly, there is a hand-held unit 244, which incorporates the microwave energy source, amplification and output circuitry. Secondly, there is a control unit 246, which contains the DC power supplies (generated from an internal 7.2 V rechargeable battery pack) and control components. Thirdly, there is a low-loss antenna 248 that is designed to provide efficient energy delivery to the treatment site (biological tissue). Finally, there is a lightweight, flexible DC feed cable 250 that allows the transfer of both DC power to the hand held unit 244 and control signals between hand held unit 244 and control unit 246 (these signals may be duplexed or conveyed using separate thin cable assemblies).

The present invention provides a pen-type generator which operates at a frequency higher than conventional small generators. For example, the microwave generator may produce a maximum power of up to 2.5 W at 14.5 GHz. Such power levels are suitable for the intended treatment applications and permit an appropriate depth of penetration of the microwave energy into the tissue. The thermal effects on the device operating at such high frequencies may need to be taken into account. For example, a cooling arrangement is described below whereby the microwave generator is cooled using a forced airflow system over the devices and a heatsink. An air inlet cone at the antenna end allows air to be drawn through small holes by a fan located at the tail end of the enclosure. Alternatively or additionally, the operator can be thermally insulated from the internal heat generated through the use of an insulated jacket.

Turning to the embodiment shown in FIG. 10, the four components identified above are now described in detail.

The hand-held unit 244 contains the main functional items that supply the microwave energy provided by the system. These items are discussed in detail in the earlier embodiments. Additional components include:

an on/off switch (e.g. push button) 252 located on a hand-held unit 244 to allow control of the application of microwave energy to the treatment site by the user. It is depressed to initiate treatment and lifted to terminate treatment.

a first status indicator 254 (e.g. LED). Under normal operating conditions, the system is self adjusting such that the magnitude of microwave energy reflected from the antenna back into the microwave source is minimized. Safety monitoring is effected by monitoring the power reflected back from the antenna. The system automatically shuts down power delivery if this exceeds a predetermined level and illuminates first status indicator 254. Once the reflected power drops below this level and the user depresses the on/off switch 252, output power delivery may resume and the first status indicator 254 is switched off.

a second status indicator 256 (e.g. another LED having a different colour from the first LED. The internal temperature of the microwave generator is monitored. Power delivery to the hand-held unit 244 is shut off automatically if the internal temperature exceeds a predetermined level. The second status indicator 256 is illuminated in this condition. Once the temperature drops below this level and the user depresses the on/off switch 252, output power delivery resumes and the second status indicator 256 is switched off.

The control unit 246 generates the DC power required by itself and the hand-held unit 244 from an internal 7.2 V rechargeable battery pack. It contains the control components (defined above) required to initialise the separate supplies in a defined sequence to ensure correct and safe start up of the microwave system. The control unit also contains:

an on/off toggle switch 258. The toggle switch 258 allows the user to switch the entire system on or off to conserve battery energy when not in use.

a reflected power indicator 260. The reflected power magnitude measured by the hand-held unit 244 is displayed on a first bar graph indicator on the control unit 246 to provide a visual indication of this level to the user and therefore a real-time assessment of system and treatment performance.

a battery status indicator 262. A second bar graph indicator on the control unit 246 provides an indication that the unit is switched on and of the level of battery energy remaining. An assessment can therefore be made as to whether to continue treatment or recharge the internal battery pack. An external charging unit may be included with the system for recharging the batteries.

The antenna 248 may be a single-use, low-loss structure (e.g. of any of the types described above) that is designed to provide efficient energy delivery to the treatment site. It is terminated with a matching tip 264 to efficiently transfer microwave radiation to the treatment site. The unit will recognise if the antenna assembly is not connected and cease power delivery accordingly.

Figure 11:
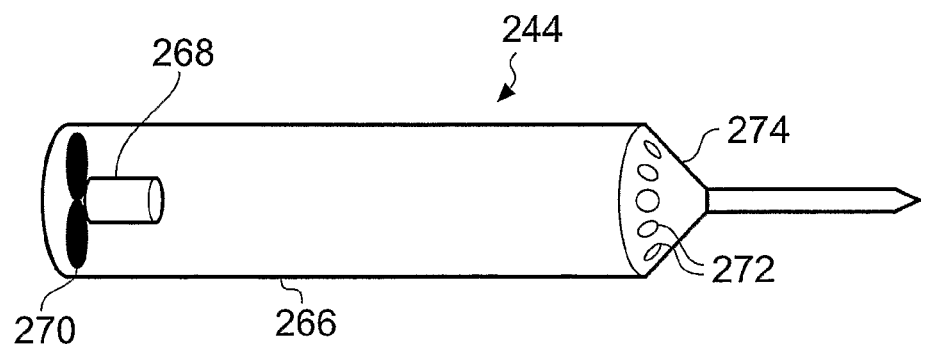
FIG. 11 shows a schematic view of a cooling arrangement for a hand held unit that is suitable for use in an embodiment of the invention.

FIG. 11 shows a cooling system for the hand-held unit 244 of FIG. 10. The microwave electronics housed inside the hand-held unit 244 is mounted on a metal heatsink to provide adequate thermal mass. However, cooling of the hand-held unit 244 may still be necessary and is achieved through a forced airflow system over the devices and heatsink. An enclosure 266 houses the mounted devices (not shown) and the airflow system.

The airflow system comprises a miniature motor 268 which drives a fan 270 at the tail (proximal) end of the enclosure 266. The fan 270 allows cool air to be drawn from the surrounding environment through small air intake holes 272 located in a cone 274 at the antenna end of the enclosure 266. This enclosure may be located within an insulated jacket (not shown) to provide thermal insulation to the user.

The invention claimed is:

1. Tissue ablation apparatus for treating biological tissue with microwave energy, the tissue ablation apparatus comprising:
    an antenna;
    a microwave generator connected to deliver microwave energy to the antenna; and
    one or more sensing elements arranged between the microwave generator and the antenna to detect a forward power level of the microwave energy delivered to the antenna and a reflected power level of microwave energy that is reflected from the antenna back towards the microwave generator,
    wherein the antenna, the microwave generator and the one or more sensing elements are integrated in a single hand held unit, and
    wherein the hand held unit includes a forced airflow system for cooling the microwave generator.

2. Apparatus according to claim 1, wherein the hand held unit comprises an elongate, pen-sized housing.

3. Apparatus according to claim 1, including a control unit connected to the hand held unit, the control unit comprising a power supply for the apparatus and a control circuit arranged to send control signals to and receive control signals from the microwave generator.

4. Apparatus according to claim 3, wherein the control unit includes a user interface for operating the apparatus.

5. Apparatus according to claim 3, wherein the control unit includes a timing circuit arranged to cause sequential operation of components in the microwave generator.

6. Apparatus according to claim 5, wherein the microwave generator includes:
    a microwave frequency source, and
    an amplifier arranged to amplify an output from the frequency source for supplying forward power to the antenna;
    and wherein the timing circuit is arranged to switch the frequency source off before switching off a drain supply to the amplifier to prevent the possibility of the frequency source turning the amplifier on.

7. Apparatus according to claim 1, wherein the microwave generator comprises:
    a microwave frequency source, and
    an amplifier arranged to amplify an output from the frequency source for supplying forward power to the antenna;
    and wherein the one or more sensing elements are in communication with the control unit such that the microwave generator is controlled on the basis of the forward power level and reflected power level detected by the one or more sensing elements.

8. Apparatus according to claim 1, wherein the microwave generator includes a modulation switch for pulsing microwave power output by the microwave generator and a power level controller for controlling the magnitude of the microwave power output by the microwave generator.

9. Apparatus according to claim 8, wherein the power level controller is arranged to attenuate the microwave power output.

10. Apparatus according to claim 8, wherein the power level controller is arranged to control an amplifying gain in the microwave generator.

11. Apparatus according to claim 1, wherein the microwave generator is operable in a high power mode suitable for ablation and a low power mode suitable for tissue type/state measurement.

12. Apparatus according to claim 1, wherein all or part of the microwave generator is mounted on a heatsink.

13. Apparatus according to claim 1, wherein the antenna is an elongate co-axial member comprising an inner conductor and an outer conductor separated by dielectric material, the inner conductor having an outer surface coated with a highly conductive material, and the outer conductor having an inner surface coated with a highly conductive material.

14. Apparatus according to claim 13, wherein the elongate co-axial member terminates at a distal end with a dielectric tip that is adapted to function as a radiating end and to create a matched condition between the co-axial member and the tissue to be treated.

15. Apparatus according to claim 1 including a tuning filter in the hand held unit arranged to dynamically match the impedance of the apparatus with the tissue to be treated.

16. Apparatus according to claim 1, wherein a visible light source is attached to the hand held unit and arranged to illuminate a treatment area that corresponds to a shape of microwave field produced by the radiating antenna.

17. Apparatus according to claim 1, wherein the hand held unit comprises an elongate enclosure having air intake holes formed therein, and the forced airflow system includes a motor arranged to drive a fan, whereby air from the surrounding environment is drawn into the enclosure to cool the microwave generator.

18. Tissue ablation apparatus for treating biological tissue with microwave energy, the tissue ablation apparatus comprising:
   a hand-held elongate enclosure having an antenna protruding from a distal end thereof, the elongate enclosure containing:
      a microwave frequency source;
      an amplifier arranged to amplify an output from the microwave frequency source and connected to supply forward power to the antenna;
      a first sensor arranged between the amplifier and the antenna to detect the magnitude of the forward power supplied to the antenna;
      a second sensor arranged between the amplifier and antenna to detect the magnitude of power that is reflected from the antenna back towards the amplifier;
      a fan; and
      a motor connected to drive the fan,
   wherein the hand-held elongate enclosure has air intake holes formed therein, whereby when the fan is driven air from the surrounding environment is drawn into the enclosure to cool the amplifier.

* * * * *